United States Patent [19]

Nowak

[11] Patent Number: 4,918,020

[45] Date of Patent: Apr. 17, 1990

[54] ANALYZING MARKER DYES IN LIQUID HYDROCARBON FUELS

[75] Inventor: Anthony V. Nowak, Fullerton, Calif.

[73] Assignee: Atlantic Richfield Company, Los Angeles, Calif.

[21] Appl. No.: 326,720

[22] Filed: Mar. 21, 1989

[51] Int. Cl.$^4$ ............................................. G01N 35/08
[52] U.S. Cl. .......................................... 436/56; 44/59; 436/60; 436/140; 436/178
[58] Field of Search ................... 436/56, 164, 174, 60, 436/139, 140, 177, 178, 92; 44/59

[56] References Cited

U.S. PATENT DOCUMENTS

| | | | |
|---|---|---|---|
| 3,862,120 | 1/1975 | Orelup | 44/59 |
| 4,009,008 | 2/1977 | Orelup | 44/59 |
| 4,049,393 | 9/1977 | Orelup | 44/59 |
| 4,209,302 | 6/1980 | Orelup | 44/59 |
| 4,735,631 | 4/1988 | Orelup | 44/59 |
| 4,764,290 | 8/1988 | Currey | 44/59 |
| 4,764,474 | 8/1988 | Orelup | 436/56 |

OTHER PUBLICATIONS

Chrompack–"Al$_2$O$_3$/KCL Plot Column"; The Analysis of Light Hydrocarbons C$_1$–C$_{10}$.

Primary Examiner—Barry S. Richman
Assistant Examiner—Amalia L. Santiago
Attorney, Agent, or Firm—John Casperson

[57] ABSTRACT

A method for analyzing marker dye present in the parts per million range in gasoline is provided using a solid-phase extraction technique with formation of the colored complex in the extraction column as well as a method for detecting the adulteration of gasoline containing the marker.

9 Claims, No Drawings

ANALYZING MARKER DYES IN LIQUID HYDROCARBON FUELS

BACKGROUND OF THE INVENTION

In one aspect, this invention relates to a method for detecting the adulteration of one liquid hydrocarbon fuel with another liquid hydrocarbon fuel. In another aspect, the invention relates to a method for analyzing a liquid hydrocarbon fuel for the presence of a marker dye.

Trademark misuse by the dealers of branded liquid hydrocarbon fuels such as gasoline is a problem for the major oil companies. Oil companies go to great expense to make sure their branded products meet stringent specifications regarding volatility and octane number, for example, as well as to provide them with effective additive packages containing detergents and the like. Consumers rely upon the trademarks to assure themselves that the product being purchased is of high quality.

Unscrupulous gasoline dealers can make large profits by selling inferior product at the price consumers are willing to pay for a high quality branded product. Large profits can also be made by unscrupulous dealers simply by diluting the branded product with an inferior product. Policing dealers who blend branded products with inferior products is very difficult in the case of gasoline because the blended products will qualitatively display the presence of each component in the branded products. The key ingredients of the branded products are generally present in such low levels that quantitative analysis to detect dilution with an inferior product is very difficult, time consuming and expensive.

Marker MP dye is a commercial product produced by Morton Chemical which can be added to liquid hydrocarbon fuels such as gasoline and used as a tracer to detect trademark violations. When added in very low amounts it is non-visible and cannot be detected by other than chemical means. It can, however, be quantified by chemical analysis to determine the degree of adulteration with non-dyed product. To detect trademark violations Morton recommends a treat level of 20 parts per million (ppm). Methodology and reagents for quantifying Marker MP dye at these treat levels are also provided by Morton. Marker MP dye is quite expensive at $36/gal. At the 20 ppm level this results in a 0.075 cent/gal. treat cost which is prohibitively expensive for many programs. Marker MP dye has also been sold in foreign countries to detect tax evasion. To detect tax evasion the dye is added to the lower taxed product and qualitatively tested for in the higher taxed product.

The recommended Morton methodology for quantification involves the extraction of the dye from the gasoline with an acidic liquid extractant using a liquid/liquid extraction technique, followed by a color forming reaction. The intensity of the color can be measured after a timed interval in a colorimeter and related to concentration. The procedure is limited in sensitivity, is time dependent, is cumbersome to perform, is subject to analyst technique variances and interferences, and is limited in sample throughput. Sample throughput is a critical parameter for large scale screening tests. The safety considerations involved in shaking gasoline with an acid extractant are also of concern. Time consuming cleanup of the extraction flasks also limits sample throughput.

OBJECTS OF THIS INVENTION

It is an object of this invention to overcome the above-noted deficiencies. In accordance with the invention, this is accomplished by use of a marker dye. In one aspect, there is provided a method for analyzing a liquid hydrocarbon for the presence of a marker dye. In another aspect, there is provided a method for detecting the adulteration with an unmarked fuel of a liquid hydrocarbon fuel which has been marked with a marker dye.

SUMMARY OF THE INVENTION

In one embodiment of the invention there is provided a method which can be employed to quantitatively detect the presence of a marker dye in a liquid hydrocarbon fuel sample. The sample to be analyzed is passed through a bed of column packing which selectively retains the marker dye on the packing. The marker dye is thereby separated from substantially the remainder of the sample. The thus separated marker dye is reacted with a color forming reagent to form a colored complex. The color intensity of the colored complex can then be related to the concentration of the marker dye in the sample.

In another embodiment of the invention there is provided a method for detecting the adulteration of a liquid hydrocarbon fuel composition containing a very low concentration of marker dye with an unmarked fuel. Prior to the discovery of an effective quantitative analytical technique for low levels of marker dye, detecting adulteration with unmarked fuel required adding on the order of 20 parts per million (ppm) of marker dye to the marked fuel. According to this embodiment of the invention, there is supplied to a service station tank a liquid hydrocarbon fuel composition which contains a low level, generally in the range from 0.05 to about 5 ppm, of marker dye. From time to time thereafter, a sample of liquid hydrocarbon fuel is drawn from the service station tank and quantitatively analyzed to determine whether the liquid hydrocarbon fuel composition so supplied to the service station tank has been diluted with liquid hydrocarbon fuel which does not contain the marker dye.

The new method of analysis is quick, easy, independent of operator variances, and adaptable to high throughput. In addition, it is capable of such high sensitivity, even in routine application, that the treat level can now be lowered to 1 ppm, resulting in a 95% reduction in dye costs. A field test with gasoline treated at the 1 ppm level has been completed to demonstrate this capability. Drastically lowered treat levels open up new possibilities for application. At this level it may be economical to treat the entire trademarked gasoline pool. The dye could easily be added to the trademarked products at the refinery (together with the additive package, for example) thus avoiding the expense of added injection equipment at terminals and providing strong evidence that certain levels of the dye should be present in the trademarked products.

In a preferred embodiment of the invention the newly developed methodology uses a technique known as Solid Phase Extraction (SPE) or sorbent extraction to selectively extract the dye from the gasoline. The extraction is carried out simply by passing a known volume of the sample gasoline through a solid phase extraction column which is a small plastic tube containing a small amount of silica to which there has been covalently bonded a chemically selective moiety. The extraction process is very selective, reproducible, and efficient, resulting in a clean separation of the dye from the gasoline matrix and from an additive package containing detergents and the like which can interfere with both the color forming reaction and with the stability of the colored complex. The Morton color forming reagent can then used to form a colored complex which can then be related to concentration of dye in the trademarked product. Multiple extractions can be carried out simultaneously if desired. For example, using the present procedure, 24 samples were processed simultaneously and extracted in a manner of 6 minutes. Further, SPE columns are disposable so there is no cleanup time involved. The extraction is very selective, and interferences are removed which results in increased time stability of the final color reaction.

DETAILED DESCRIPTION OF THE INVENTION

U.S. Pat. No. 4,209,302, issued June 24, 1980 to Orelup, the disclosure of which is incorporated by reference, discloses marker dyes which can be usefully employed in accordance with the invention. Generally speaking, these dyes comprise 1-(amino)-3-(alpha or beta naphthylamino)-propanes. The amine at the one position can be a secondary or tertiary amine and may be part of a ring structure. The preferred marker dye used in the invention is selected from the group consisting of 1-(4-morpholino)-3-(alpha naphthylamino)-propane and 1-(4-morpholino)-3(beta naphthylamino)-propane.

The marker dye forms a colored complex when it is reacted with a color forming reagent. Generally speaking, diazotized aromatic amines are suitable color forming reagents. The preferred color forming reagent used in the invention contains 2-chloro-4-nitroaniline as the reactive ingredient. Preferably, the color forming reagent is solubilized, stored and used in glacial acidic acid.

The bed of column packing through which the sample of liquid hydrocarbon fuel is passed is mostly silica powder, to which there has been applied a moiety which is chemically selective for the marker dye. The chemically selective moiety is covalently bonded to the silica. The chemically selective moiety bonded to the silica preferably comprises a strong anion exchange (SAX) phase. Suitably treated packings are commercially available from a number of sources.

The preferred technique to use in accordance with the invention is to pass the sample of liquid hydrocarbon fuel containing the marker dye through the bed of column packing. The preferred technique uses solid phase extraction to selectively extract the dye from the liquid sample. Preferably, the technique is used with petroleum derived hydrocarbon fuels because such fuels have been marked and tested with good results. It is believed that the technique will be applicable to gasoline, kerosene, diesel and jet fuels, for example. The marker dye will generally be present in the fuel at a level in the range from about 0.05 to 5 parts per million (ppm), based on total weight of hydrocarbon fuel containing the marker dye. The method could also be applied to even lower levels of marker dyes but passing increasingly larger samples through the bed would be required. Preferably, the liquid hydrocarbon fuel contains the marker dye in the range of about 0.2 to about 2 parts per million because gasoline containing the marker dye at a level closely encompassed by this range has been quantitatively analyzed for marker dye with good results.

As the sample is passed through the bed of column packing, the marker dye is retained on the packing and is thereby separated from substantially the remainder of the liquid hydrocarbon fuel. Best results have been obtained when the packing has been preconditioned with an acid buffer solution. A buffer solution with a pH of about 2 has been used with good results.

After the separation, the marker dye is reacted with the color forming reagent. Although the marker dye could be reacted outside of the column, after removal from the packing by an eluant liquid, good results have been obtained by reacting the marker dye with the color forming reagent in the column, thereby avoiding dilution of the marker dye with the eluant liquid prior to reaction with the color forming reagent. Even better results are obtained when the column is dried prior to addition of the color forming reagent because the last traces of gasoline are removed and color-forming reaction can then be made to occur under even more concentrated conditions and the colored complex can be recovered in concentrated form.

In a preferred embodiment of the invention, the colored complex is eluted from the column in an eluant liquid and the eluant liquid containing the colored complex is introduced into a colorimeter tube and analyzed for intensity. A 2% aqueous solution of methane sulfonic acid comprises the preferred eluant liquid because it seems to stabilize the colored complex. Determining the color intensity of the colored complex is preferably conducted spectrophotometrically on the solution containing the colored complex after elution from the column. The signal produced will be representative of the concentration of the marker dye in the sample of the hydrocarbon fuel from which the marker dye is separated.

The most unique aspects of the preferred method, and the ones which clearly differentiate it from standard practice, involves both the selection of the SPE column and also the manner in which the color forming reaction is performed. Conventional thinking would suggest that either polar or non-polar bonded phase columns be used to affect the desired separation. Some of these can perform the separation but additives and other gasoline components are also retained such that problems result with the subsequent formation and stability of the colored complex. The invention uses ion-exchange bonded phase columns to cleanly and efficiently separate the dye from the gasoline matrix. Ion exchange mechanisms are ordinarily thought of as being limited to aqueous environments. Under the chosen conditions of the extraction, however, the dye is believed to develop sufficient ionic character such that a "pseudo" ion exchange mechanism prevails, enabling the separation to occur.

After extraction, the dye is believed to reside as a very thin layer firmly bound to the SAX bonded phase. The Morton color forming reagent is preferably added directly to the column where the color reaction occurs. This provides a number of significant advantages. First, it facilitates selectively removing the dye from the column. It also enables the color forming reaction to occur in a very small volume with concentrated reagent. The rate of the color forming reaction is increased thereby decreasing the time dependence of the reaction and enabling the rapid measurement of the color intensity after elution of the complex from the column.

Because the technique gives highly accurate quantitative results even for very low levels of marker dye, on the order of one part per million, it makes possible a method for detecting the adulteration of a liquid hydrocarbon fuel composition with good economy. In accordance with this embodiment of the invention, there is supplied to a service station tank a liquid hydrocarbon fuel composition containing a known concentration of the marker dye. From time to time, generally after the lapse of several hours or a few days, a sample of liquid hydrocarbon fuel is withdrawn from the service station tank and quantitatively analyzed, preferably by absorption, to determine whether the liquid hydrocarbon fuel containing the marker dye has become diluted with a hydrocarbon fuel composition which does not contain the marker dye during the intervening period. It is expected that very good and economical results can be obtained when the marker dye is present at a known concentration in the range of between 0.2 and about 2 parts per million. The absorption can be related to the concentration of marker dye in the recovered sample by comparison with standards of known concentration.

The marker dye can be added to the liquid hydrocarbon fuel by batch or continuous means, as desired. Preferably, the marker dye is added to the liquid hydrocarbon fuel using existing equipment at the same time as the usual additive package. The invention is further illustrated by the following example.

"TYPICAL" EXAMPLE

Sorbent extraction, the process used to separate the Marker MP dye from the gasoline is a physical process involving a liquid phase (gasoline) and a solid phase (the silica based column packing). In sorbent extraction, the solid phase has a greater attraction for the isolate (Marker MP dye) than the liquid phase (gasoline) in which it is dissolved. As the gasoline solution is passed through the column the Marker dye is removed from the gasoline and retained on the column.

The column packing material consists of a bonded phase silica based sorbent. The specific properties of a given bonded silica sorbent are a result of the functional group covalently bonded to the silica substrate. A variety of different bonded silicas are commercially available, offering a wide range of selective properties for extraction. Bonded silicas are formed by the reaction of organosilanes with activated silica. The product is a sorbent with the functional group of the organosilane (in the case of the SAX this is a trimethylaminopropyl group) attached to the silica substrate through a silyl either linkage.

The bonded phase material used in the Marker MP dye extraction work is a commercial product produced by several different sources. A SAX material was used consisting of 500 mg. of bonded phase in a polyethylene column with an internal volume of 2.8 ml. It has a porosity of 60 Angstroms. Particle size is 40 microns. The material is held in the column with two polyethylene frits.

A sample of gasoline (2.5–20 ml.) is passed through the above-described column which has been preconditioned with 2 ml. of a pH 2 buffer solution. 2.5 ml. of hexane is then rinsed through the column, after which air is pulled through the column for ca. 2 minutes to dry it. 100 ul. of the Morton Reagent DII is added to the column to form a colored complex. The colored complex is then eluted with 2.5 ml. of 2% methane sulfonic acid directly into a round colorimeter tube. The absorbance of the solution is measured at 530 nanometers (nm). Determination of marker concentration in the sample is by reference to a calibration curve prepared by taking known standards through the above procedure.

PROCEDURAL DETAILS OF A PREFERRED METHOD

1. It is convenient to process 6–24 samples in a batch mode in a VacElut SPS 24 sample processing station. Place 6–24 SAX columns in a test tube holder and with a re-pipet add 2 ml. of a pH2 buffer solution to each.

2. Fit a 5 ml. Luer-Lok disposable syringe (with its plunger extended) to the end of the column and by slowly pushing on the plunger to its end of travel, displace the buffer from the column. The column is now properly conditioned for use. Remove the syringe and do the same for each column in turn.

3. Fit a 5–20 ml. Luer-Lok disposable syringe (outer cylinder only) to the end of each SPE column to act as a sample reservoir, and place each in an inlet of the vacuum elution apparatus, after first insuring that the vacuum is turned off.

4. Add 2–20 ml. of gasoline sample to each reservoir in turn with a syringe. After all samples are added, open and adjust the vacuum inlet valve to begin sample flow. The sample should be introduced in a dropwise fashion to column, over the period of 1–6 minutes, depending on sample size.

5. Continue the air flow through the column for one minute after all the sample has passed through.

6. Turn off vacuum to the elution device and vent it.

7. With a re-pipet add 2.5 ml. of hexane to each column. Open the vacuum valve and allow air to be pulled through the columns for ca. 2 minutes after the hexane passes through to dry the columns.

8. Close off the vacuum valve.

9. Remove the sample reservoirs from the columns.

10. Add 100 ul. of Reagent DII to each column with a micro dispenser. Touch the column first with the tip of the pipe before dispensing to evenly disperse the reagent. Allow the color formation reaction to proceed for 3 minutes.

11. Add 2.5 ml. of a 2% methane sulfonic acid solution to each column from a re-pipet.

12. Remove a column from the elution device and fit a 5 ml. Luer-Lok disposable plastic syringe with its plunger extended to the end of the column. By pushing on the plunger to its end of travel displace the colored complex solution directly into a round colorimeter tube. Cap the end of the tube with a disposable cap and gently shake the tube to mix the solution.

13. Perform step 12 for each column in turn.

14. Insert each tube in a spectrophotometer and read the absorbance at 530 (nm). Use water as a reference.

15. Relate absorbance to concentration by reference to a calibration curve prepared using standards and the above procedure.

16. Begin the next set of samples as per Step 1.

Note: If the spectrophotometer uses 1 cm. square cuvettes, a transfer step is required. The colored complex must first be eluted into a test tube for mixing, then transferred to the square 1 cm. cell for the absorbance measurement.

What is claimed is:

1. A method for determining the concentration of a marker dye in a liquid hydrocarbon fuel, said method comprising:

a. passing a sample of a liquid hydrocarbon fuel containing a marker dye through a bed of column packing to selectively retain the marker dye on the column packing and thereby substantially separate the marker dye from the liquid hydrocarbon fuel;

b. reacting the thus separated marker dye with a color forming reagent to form a colored complex; and c. determining a color intensity for the colored complex, said color intensity being indicative of the concentration of the marker dye inserted after "complex".

2. A method as in claim 1 wherein the column packing is formed from silica to which there has been covalently bonded a chemically selective moiety.

3. A method as in claim 2 wherein the chemically selective moiety comprises a strong anion exchange moiety, said method further comprising drying the column after step a.

4. A method as in claim 3 further comprising preconditioning the column packing with an acid buffer, wherein the strong anion exchange moiety comprises trimethylaminopropyl groups.

5. A method as in claim 3 wherein the thus separated marker dye is contacted on the column packing with a concentrated solution of the color forming reagent after the drying step.

6. A method as in claim 1 wherein the color intensity for the colored complex is determined spectrophotometrically on a solution containing the colored complex, said method further comprising producing a signal which is representative of the concentration of marker dye in the sample of hydrocarbon fuel from which the marker dye was separated.

7. A method as in claim 5 further comprising eluting the colored complex from the column packing in an eluant liquid and introducing the eluant liquid and colored complex into a colorimeter tube, wherein the marker dye is selected from the group consisting of 1-(4-morpholino)-3-(alpha naphthylamino)-propane and 1-(4-morpholino)-3-(beta naphthylamino) propane, the color forming reagent comprises 2-chlor-4-nitroaniline solution, and the marker dye is present in the sample at a concentration in the range of 0.05–5 ppm.

8. A method for detecting adulteration of a liquid hydrocarbon fuel composition; said method comprising:

a. supplying a liquid hydrocarbon fuel composition containing a known concentration in the range of from 0.2 to 2 ppm of a marker dye selected from the group consisting of 1-(4 morpholino)-3-(alpha napthylamino)-propane and 1-(4-morpholino)-3-(beta napthylamino) propane to a service station tank; and b. from time to time withdrawing a liquid hydrocarbon fuel sample from the service station tank and quantitatively analyzing said sample to determine whether the liquid hydrocarbon fuel containing the marker dye and supplied to the service station tank in step (a) has become diluted with a hydrocarbon fuel composition which does not contain the marker dye;

wherein the dye is separated from the sample by retention in a solid phase extraction column and is contacted with a color-forming reagent while in the column to form a colored complex which is in turn eluted from the column in an eluant liquid which is analyzed spectrophotometrically for absorbance at 530 nm.

9. A method for detecting adulteration of a liquid hydrocarbon fuel composition; said method comprising:

a. supplying a liquid hydrocarbon fuel composition containing a known concentration in the range of 0.05 to 5 ppm of a marker dye to a service station tank; and b. from time to time withdrawing a liquid hydrocarbon fuel sample from the service station tank and quantitatively analyzing said sample to determine whether the liquid hydrocarbon fuel containing the marker dye and supplied to the service station tank in step (a) has become diluted with a hydrocarbon fuel composition which does not contain the marker dye;

wherein the dye is separated from the sample by retention in a solid phase extraction column and is contacted with a color-forming reagent while in the column to form a colored complex which is in turn eluted from the column in an eluant liquid which is analyzed spectrophotometrically for absorbance at 530 nm.

* * * * *

UNITED STATES PATENT AND TRADEMARK OFFICE
CERTIFICATE OF CORRECTION

PATENT NO. : 4,918,020
DATED : 04/17/90
INVENTOR(S) : Anthony V. Nowak

It is certified that error appears in the above-identified patent and that said Letters Patent is hereby corrected as shown below:

In Column 7, line 10, insert a period after the word "dye"; and
line 10-11, delete the phrase "inserted after "complex","

Signed and Sealed this

Sixteenth Day of April, 1991

*Attest:*

HARRY F. MANBECK, JR.

*Attesting Officer*      *Commissioner of Patents and Trademarks*